United States Patent [19]
Meulemans et al.

[11] Patent Number: 5,990,159
[45] Date of Patent: Nov. 23, 1999

[54] USE OF 5HT4 RECEPTOR ANTAGONISTS FOR OVERCOMING GASTROINTESTINAL EFFECTS OF SEROTONIN REUPTAKE INHIBITORS

[75] Inventors: Ann Louise Gabriëlle Meulemans, Mol; Jean-Paul René Marie AndréBosmans, Rijkevorsel, both of Belgium

[73] Assignee: Janssen Pharmaceutica, N.V., Beerse, Belgium

[21] Appl. No.: 09/117,974

[22] PCT Filed: Feb. 7, 1997

[86] PCT No.: PCT/EP97/00586

§ 371 Date: Aug. 11, 1998

§ 102(e) Date: Aug. 11, 1998

[87] PCT Pub. No.: WO97/29739

PCT Pub. Date: Aug. 21, 1997

[30] Foreign Application Priority Data

Feb. 15, 1996 [EP] European Pat. Off. .............. 96200380

[51] Int. Cl.⁶ .......................... A61K 31/34; A61K 31/135
[52] U.S. Cl. ............................. 514/469; 514/651
[58] Field of Search ...................... 514/469, 651

[56] References Cited

FOREIGN PATENT DOCUMENTS

| | | |
|---|---|---|
| WO 9200103A | 1/1992 | WIPO . |
| WO 9400113A | 1/1994 | WIPO . |
| WO 9408998A | 4/1994 | WIPO . |
| WO 9427987A | 12/1994 | WIPO . |
| WO 9504737A | 2/1995 | WIPO . |

OTHER PUBLICATIONS

Chemical Abstracts, vol. 122, No. 15, Apr. 10, 1995, Abstract No. 178309, A. Lucchelli et al.: "The interaction of antidepressant drugs with central and peripherical enteric 5–HT3 and 5–HT4 receptors".

*Primary Examiner*—Raymond Henley, III
*Attorney, Agent, or Firm*—Ellen Ciambrone Coletti

[57] ABSTRACT

The present invention concerns the use of receptor antagonists of the 5HT4 receptor for avoiding, alleviating, suppressing or overcoming the gastrointestinal side-effects of serotonin reuptake inhibitors. The present invention also concerns pharmaceutical formulations comprising 5HT4-receptor antagonists for alleviating, suppressing or overcoming the gastrointestinal side-effects of serotonin reuptake inhibitors, as well as pharmaceutical compositions comprising 5HT4 receptor antagonists and serotonin reuptake inhibitors.

11 Claims, 8 Drawing Sheets

USE OF 5HT4 RECEPTOR ANTAGONISTS FOR OVERCOMING GASTROINTESTINAL EFFECTS OF SEROTONIN REUPTAKE INHIBITORS

This application is the national stage of application no. PCT/EP97/00586, filed Feb. 7, 1997, which application claims priority from EP 96.200.380.2, filed Feb. 15, 1996.

The present invention concerns the use of antagonists of the 5HT4 receptor for avoiding, alleviating, suppressing or overcoming the gastrointestinal side-effects of (selective) serotonin reuptake inhibitors. The present invention also concerns pharmaceutical formulations comprising 5HT4-receptor antagonists and serotonin reuptake inhibitors for avoiding, alleviating, suppressing or overcoming the gastrointestinal side-effects of serotonin reuptake inhibitors.

Depression in its many variations has recently become much more visible to the general public than it has previously been. It is now recognized as an extremely damaging disorder, and one that afflicts a surprisingly large fraction of the population. Suicide is the most extreme symptom of depression, but many people, not so drastically afflicted, live in misery and partial or complete uselessness, which may also afflict their family.

Depression is often associated with other diseases or conditions, or caused by such other conditions. For example, it is associated with Parkinson's disease; with HIV infection; with Alzheimer disease; and with abuse of anabolic steroids. Depression may also be associated with abuse of any substance, or may be associated with behavioral problems resulting from or occuring in combination with head injuries, mental retardation or stroke (EP 0714663).

During the last two decades, the treatment of depression with antidepressants has moved from the treatment of hospitalised melancholic inpatients to the outpatient setting. During the last few years, the majority of depressed patients, including patients with moderate or mild depressive symptoms, are now treated in primary care. Recent studies have shown that mild depression is a serious condition, representing social and economical liability to the patient and a high cost to society. Such patient clearly benefits from therapy with antidepressants. One of the main contributing factors to this evolution in therapeutic practice has been the introduction of new antidepressants, among which the selective serotonin reuptake inhibitors (SSRIs) are the most important and most widely prescribed. Although the SSRIs are said to have a lesser incidence of side effects, still the use of SSRIs is hampered by a number of adverse effects. The adverse effects occurring most frequently during treatment with SSRIs are gastrointestinal disturbances, such as, for example nausea, diarrhoea/loose stools, constipation, with an incidence of 6 to 37% (Drugs 43 (Suppl. 2), 1992). Nausea is the main adverse effect in terms of incidence. These adverse effects, although mild to moderate in severity, shy some patients away from treatment with SSRIs. The percentage of patients withdrawing because of nausea ranges from 3 to 8% of the patients. Moreover it has been frequently observed that after administration of SSRIs, patients suffer from dyspepsia.

We discovered that the gastrointestinal disturbances associated with the administration of SSRIs is mainly due to a diminished compliance of the stomach. The "compliance of the stomach" can be expressed as the ratio of the volume of the stomach over the pressure exerted by the stomach wall. The compliance of the stomach relates to the gastric tone, which is the result of the tonic contraction of muscle fibers of the proximal stomach. This proximal part, by exerting a regulated tonic contraction (gastric tone), accomplishes the reservoir function of the stomach, namely gastric accommodation and emptying. Impairment of adaptive relaxation as a response to food intake may be the pathophysiological basis of some gastrointestinal disturbances or disorders associated with the use of SSRIs.

Patients suffering from dyspepsia after the intake of SSRIs feel hungry but cannot finish a normal meal. This is explained by this diminished stomach compliance. Normally when a subject starts eating, the stomach will show an adaptive relaxation, i.e the stomach will relax to accept the food that is ingested. This adaptive relaxation is not possible when the stomach compliance is hampered.

The problem to be solved is to provide a means for avoiding, alleviating, suppressing or overcoming the gastrointestinal disturbances which are associated with the intake of SSRIs, i.e to normalize the compliance of the stomach by reducing the gastric tone to a normal level.

Unexpectedly, we have found that 5HT4 receptor antagonists can normalise the diminished stomach compliance caused by the administration of SSRIs, thus avoiding, alleviating, suppressing or overcoming the gastrointestinal disturbances caused by the administration of SSRIs. It should be noted that the 5HT4 receptor antagonists do not as such influence the stomach compliance, they only seem to antagonise the effect on the stomach caused by the SSRIs.

Hence, there is provided the use of a 5HT4 receptor antagonist for the manufacture of a medicament to avoid, alleviate, suppress or overcome the gastrointestinal disturbances caused by SSRIs. Also provided is a method of avoiding, alleviating, suppressing or overcoming the gastrointestinal disturbances of SSRIs.

The term "selective serotonin reuptake inhibitors" as used herein refer to compounds that selectively inhibit the (re-)uptake of serotonin. Relevant tests to determine whether a compound is a selective serotonin reuptake inhibitor are known in the art (for an overview see Life Sciences, 57, 411–441,1995).

The term "selective serotonin reuptake inhibitors" or "SSRIs" will both be used hereinunder. The terms refer to the compounds as such or where appropriate to the pharmaceutically acceptable acid or base addition salts thereof or, again where appropriate, to stereochemically isomeric forms thereof.

The term "5HT4 receptor antagonist" refers to the compounds as such or where appropriate to the pharmaceutically acceptable acid or base addition salt thereof or, again appropriate, to stereochemically isomeric forms thereof.

The pharmaceutically acceptable acid addition salts as mentioned hereinabove are meant to comprise the therapeutically active non-toxic acid addition salt forms which the compounds are able to form. The compounds which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The pharmaceutically acceptable addition salts as mentioned hereinabove are meant to comprise the therapeutically active non-toxic base addition salt forms which the compounds are able to form. Examples of such base addition salt forms are, for example, the sodium, potassium, calcium salts, and also the salts with pharmaceutically acceptable amines such as, for example, ammonia, alkylamines, benzathine, N-methyl-D-glucamine, hydrabamine, amino acids, e.g. arginine, lysine.

The term addition salt as used hereinabove also comprises the solvates which the compounds as well as the salts thereof, are able to form. Such solvates are for example hydrates, alcoholates and the like.

The term stereochemically isomeric forms as used hereinbefore defines the possible different isomeric forms which the compounds may possess.

The term "selective serotonin reuptake inhibitors" or "SSRIs" may also refer to prodrugs or forms that may release the actual active ingredient.

Selective Serotonin Reuptake Inhibitors are, for instance, fluvoxamine, fluoxetine, paroxetine, sertraline, citalopram, venlafaxine, cericlamine, duloxetine, milnacipran, nefazodone, cyanodothiepin, CGP-6085-A, FG-7080, LY-280253, LY-285974 or RP 68303. (This list is not meant to be exhaustive). An overview of these selective serotonin Reuptake Inhibitors is, for instance, provided in The Year Drugs News, 1995 Edition, pages 47 and 48 by Prous J. R. CGP-6085-A is 4-(5,6-dimethyl-2-benzofuranyl) piperidine HCl and was first mentioned in Eur. J. Pharmacol., 46, 387 (1977).

The term "5HT4 receptor antagonist" as used herein refers to a compound which binds to the 5HT4 receptor as defined by the IUPHAR (see Pharmacological Reviews, 1994, 44, 157–203) and that antagonises the effect of a 5HT4 agonist. Relevant test to determine whether or not a compound is a 5HT4 receptor antagonist is the "Guinea-pig distal colon"-test as described in Br. J. Pharm. (1993), 1593–1599 or in the test described in Arch. Pharmacol. (1991) 343, 439–446.

The following compounds are known 5HT4 receptor antagonists (This list is not exhaustive):

A-85380 (Abbott Laboratories) (WO 9408994)
SB 204070 (SmithKlineBeecham) (Drugs Fut. (1994) 19: 1109–1121),
SB 207226 (SmithKlineBeecham) (Marketletter 22-1 22 en 22-18 (1995)),
SB 207058 (SmithKlineBeecham) (Exp Opin Invest Drugs (1994) 3(7): 767),
SB 207710 (SmithKlineBeecham) (Drug Data Report (1993) 15 (10): 949),
SB 205800 (SmithKlineBeecham) (Drug Data Report (1993) 15 10): 949),
SB 203186 (SmithKlineBeecham) (Br J Pharmacol (1993) 110: 1023–1030),
SDZ 205557 (Sandoz) (Eur J Pharmacol (1992) 211: 1),
N 3389 (Nisshin Flour Milling) (Eur J Pharmacol (1994) 271: 159),
FK 1052 (Fujisawa) (J Pharmacol Exp Ther (1993) 265: 752),
SC 56184 (Searle) (R&D Focus (1993) 2(37) 10),
SC 53606 (Searle/Monsanto) (J Pharmacol Exp Ther 226: 1339),
DAU 6285 (Boerhinger Ingelheim) (Br J Pharmacol (1992) 105: 973),
GR 125487 (Glaxo) (Br J Pharmacol (1994) 113 suppl. 119P & 120P),
GR 113808 (Glaxo) (Br J Pharmacol 110: 1172),
RS 23597 (Syntex) (Bioorg Med Chem Lett (1994) 4(20): 2477),
RS 39604 (Syntex) (Br J Pharmacol (1995) 115, 1087–1095),
LY-353433 (Eli Lilly Co Ltd) (J. Pharmacol. Exp. Ther. (1996), 277(1), 97–104),
R 50595 (Eur. J. Pharmacol., 212 (1992), 51–59)

In view of their useful pharmacological properties, both the subject 5HT4 receptor antagonists and the selective serotonin reuptake inhibitors may be formulated into various pharmaceutical forms for administration purposes.

The 5HT4 receptor antagonist and the SSRI may be present in the same pharmaceutical dosage form, for instance, in the same tablet. In such a case the 5HT4 receptor antagonist and the SSRI are evidently administered simultaneously. Of course, the 5HT4 receptor antagonist may also be formulated separately from the SSRI. However, it may be advantageous to put the 5HT4 receptor antagonist unit dosage form and the SSRI unit dosage form in the same package, more particularly, in the same blister. For instance, blisters may be sold wherein a row of 5HT4 receptor antagonist tablets is along side a row of SSRI tablets.

The present invention thus encompasses a product containing a 5HT4 receptor antagonist and a SSRI as a combined preparation for simultaneous, separate or sequential use in antidepressant therapy.

To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The dosages of respectively the 5HT4 receptor antagonist as well as the selective serotonin reuptake inhibitor are set by the physician who is treating a particular patient.

Dosage guidelines for some of the drugs can already be found in literature. For some of the SSRIs the following dosage guidelines apply.

Citalopram: from about 5 to about 50 mg once/day; preferred, from about 10 to about 30 mg once/day;

fluvoxamine: from about 20 to about 500 mg once/day; preferred, from 50 to about 300 mg once/day;

paroxetine: from about 5 to about 100 mg once/day; preferred, from about 5 to about 300 mg-once/day.

Those skilled in the art could easily determine the effective amount for the 5 HT4 receptor antagonist from the test results presented hereinafter. In general it is contemplated that an effective amount of a 5HT4 receptor antagonist would be from 0.001 mg/kg to 10 mg/kg body weight, and in particular from 0.04 mg/kg to 1 mg/kg body weight. It may be appropriate to administer the required dose as two, three, four or more sub-doses at appropriate intervals throughout the day. Said sub-doses may be formulated as unit dosage forms, for example, containing 0.01 to about 250 mg, interestingly from 0.01 to about 100 mg, and in particular 0.1 mg to 10 mg of 5HT4 receptor antagonist per unit dosage form.

The following combinations of SSRI and 5HT4 receptor antagonist are envisaged as interesting:

citalopram/GR 125487;
fluvoxamine/GR 125487
paroxetine/GR 125487
fluoxetine/GR 125487
citalopram/SB 204070;
fluvoxamine/SB 204070
paroxetine/SB 204070
fluoxetine/SB 204070

A preferred combination formulation would be fluvoxamine as SSRI and GR 125487 as 5HT4 receptor antagonist.

In general, the treating physician would create a combination of the present invention by choosing a dosage for a certain SSRI and choosing a dosage of the 5HT4 receptor antagonist in the general range of from about 1 to about 250 mg/dose. More preferred dosages, depending on the compound would be from about 1 to about 100 mg/dose.

The adjunctive therapy of the present invention is carried out by administering a first component with one of the second component compounds in any manner which provides effective levels of the two compounds in the body at the same time.

It should be noted that the 5 HT4 receptor antagonists can also be used as a profylactic treatment, i.e. a patient can take in first the 5 HT4 receptor antagonist and subsequently take in the SSRI, thus avoiding the gastrointestinal side-effects altogether.

Pharmacological Example

Gastric Tone Measured by an Electronic Barostat in Conscious Dogs

Gastric tone cannot be measured by manometric methods. Therefore an electronic barostat was used. This allows the study of the physiological pattern and regulation of gastric tone in conscious dogs and the influence of test-compounds on this tone.

The barostat consists of an air injection system which is connected by a double-lumen 14-French polyvinyl tube to an ultrathin flaccid polyethylene bag (maximal volume: ±700 ml). Variations in gastric tone were measured by recording changes in the volume of air within an intragastric bag, maintained at a constant pressure, or at varying pressure levels. The barostat maintains a constant pressure (preselected) within a flaccid air-filled bag introduced into the stomach, changing the volume of air within the bag by an electronic feedback system.

Thus, the barostat measures gastric motor activity (contraction or relaxation) as changes in intragastric volume (decrease or increase resp.) at a constant intragastric pressure. The barostat consists of a strain gauge linked by an electronic relay to an air injectionaspiration system. Both the strain gauge and the injection system are connected by means of double-lumen polyvinyl tube to an ultrathin polyethylene bag. A dial in the barostat allows selection of the pressure level to be maintained within the intragastric bag.

Female beagle dogs, weighing 7–17 kg, were trained to stand quietly in Pavlov frames. They were implanted with a gastric cannula under general anaesthesia and aseptic precautions. After a median laparotomy, an incision was made through the gastric wall in longitudinal direction between the greater and the lesser curve, 2 cm above the nerves of Latarjet. The cannula was secured to the gastric wall by means of a double purse string suture and brought out via a stub wound at the left quadrant of the hypochondrium. Dogs were allowed a recovery period of two weeks.

At the beginning of the experiment, the cannula was opened in order to remove any gastric juice or food remnants. If necessary, the stomach was cleansed with 40 to 50 ml lukewarm water. The ultrathin bag of the barostat was positioned into the fundus of the stomach through the gastric cannula. In order to ensure easy unfolding of the intragastric bag during the experiment, a volume of 150–200 ml was injected into the bag by raising the pressure to maximally 14 mm Hg (about 1.87 kPa) very briefly. This procedure was repeated twice. A stabilisation period of 1 hour was allowed.

After a stabilization period of 30 minutes at an intragastric pressure of 2 mmHg (about 0.27 kPa), pressure-volume curves were constructed by increasing intragastric pressure with 2 mm Hg (0.27 kPa ) steps (maximally 14 mm Hg(about 1.87 kPa)) (11 min at 2 mmHg (0.27 kPa ) and 3 min at each pressure step). These changes in pressure could be set either manually or could be installed via a computer program (lab view). At least 2 stable curves had to be observed before drug administration.

Then, the test compound was administered subcutaneously between the first 3–5 minutes at 2 mmHg (0.27 kPa). Test compounds were screened at 0.63 mg/kg s.c. Other doses and routes were tested if a testcompound was shown to be active during the screening procedure. Four new pressure-volume curves were then constructed to evaluate the effect induced by the compound.

BRIEF DESCRIPTION OF THE FIGURES

Further elaboration of the information in the figures:

First fluvoxamine is administered subcutaneously and a diminished compliance can be observed as can be seen from FIG. 1. The curve "before" refers to the measurements before administration of the fluvoxamine. The curve "after" refers to the measurements in the stomach after administration of fluvoxamine. FIG. 1 clearly shows that the gastric tone remains high in comparison with the control experiment ("before") when increasing the pressure.

FIGS. 2 to 5 show an analogous behaviour of the gastric tone when other SSRIs are admininistered. The effect is shown for citalopram (FIG. 2), paroxetine (FIG. 3), fluoxetine (FIG. 4) and CGP-6085-A (FIG. 5).

FIG. 6 shows that GR 125487 (a 5HT4 receptor antagonist) does not influence the gastric tone at all. The curve for the control experiment coincides with the curve obtained after administration of GR 125487 (0.04 mg/kg s.c.).

FIG. 7 demonstrates that GR 125487 (0.04 mg/kg s.c.) (a 5HT4 receptor antagonist) can normalise the gastric tone of a dog which was pretreated with fluvoxamine (0.63 mg/kg s.c.) (a SSRI). The curve of gastric tone after treatement with GR 125487 of a dog was pretreated with fluvoxamine (a SSRI) is not significant different from the curve of control.

FIG. 8 demonstrates that GR 125487 (0.04 mg/kg s.c.) (a 5HT4 receptor antagonist) avoids that the gastric tone of a dog becomes influenced by fluvoxamine. The curve of gastric tone after first treatment with GR 125487 and subsequent treatment with fluvoxamine (0.63 mg/kg s.c.)

COMPOSITION EXAMPLES

Figure 1:
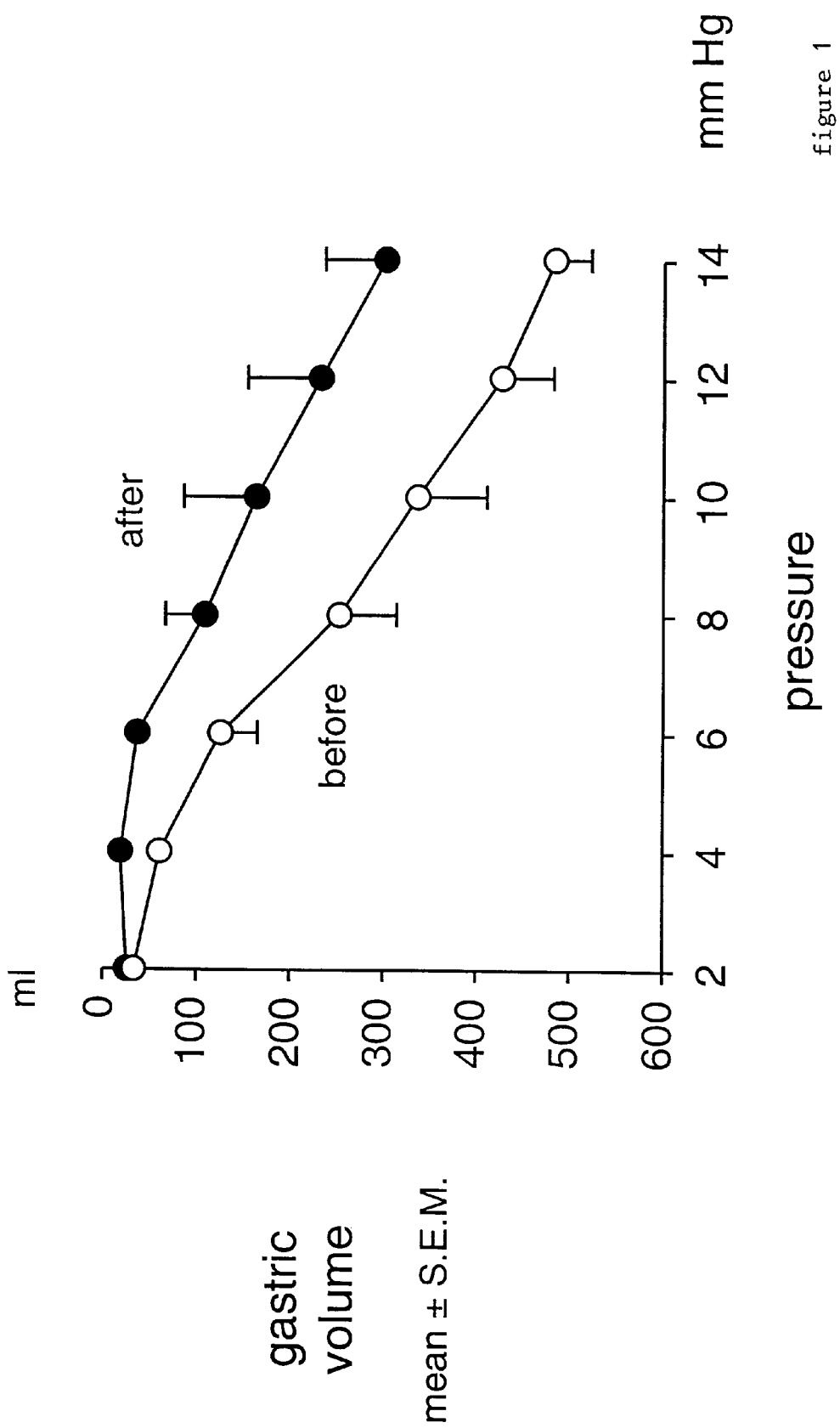
FIG. 1 Effect of fluvoxamine (0.63 mg/kg s.c.) on gastric relaxation induced by changes in pressure in conscious dogs. (n=4)
Figure 2:
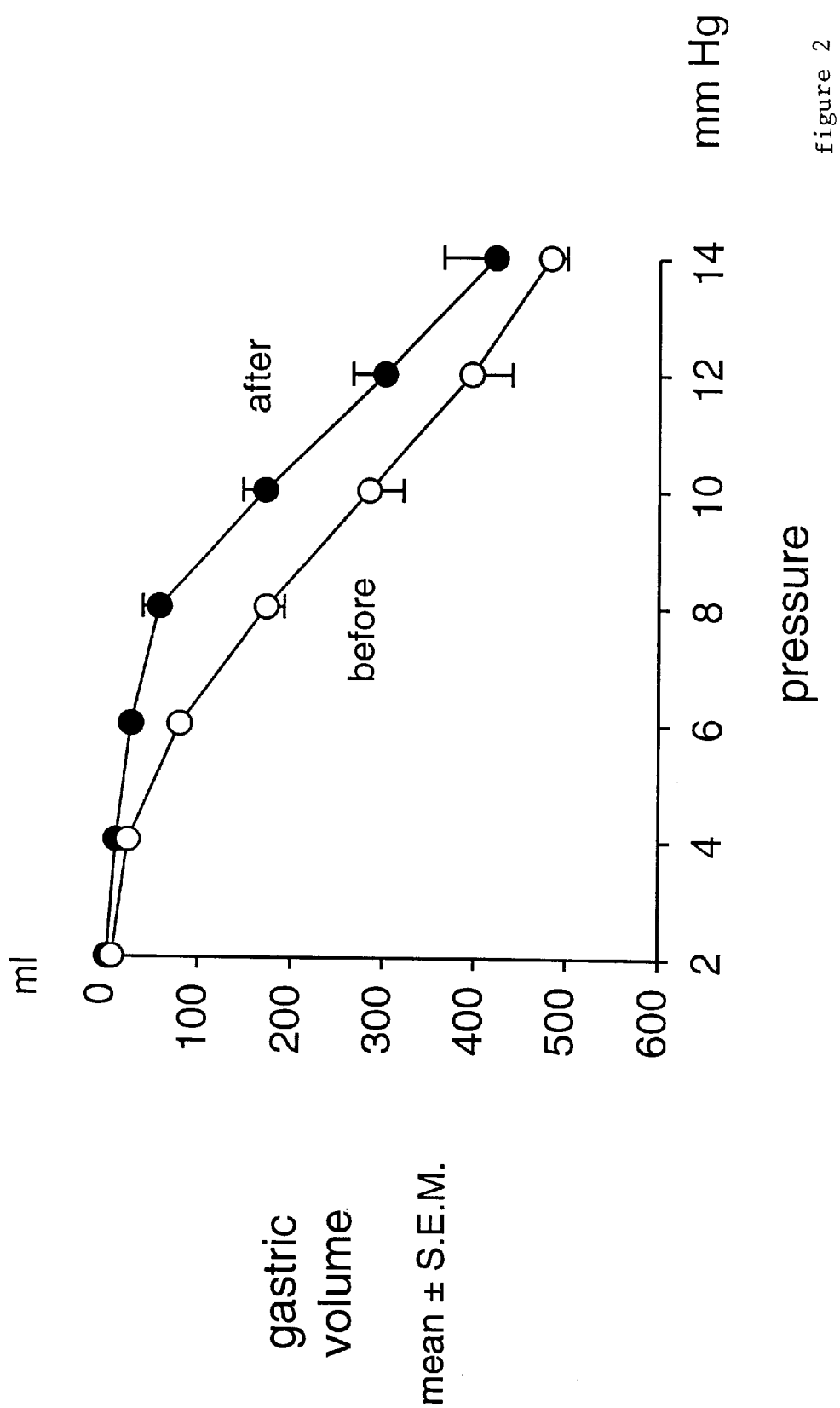
FIG. 2 Effect of citalopram (0.63 mg/kg s.c.) on gastric relaxation induced by changes in pressure in conscious dogs. (n=4)
Figure 3:
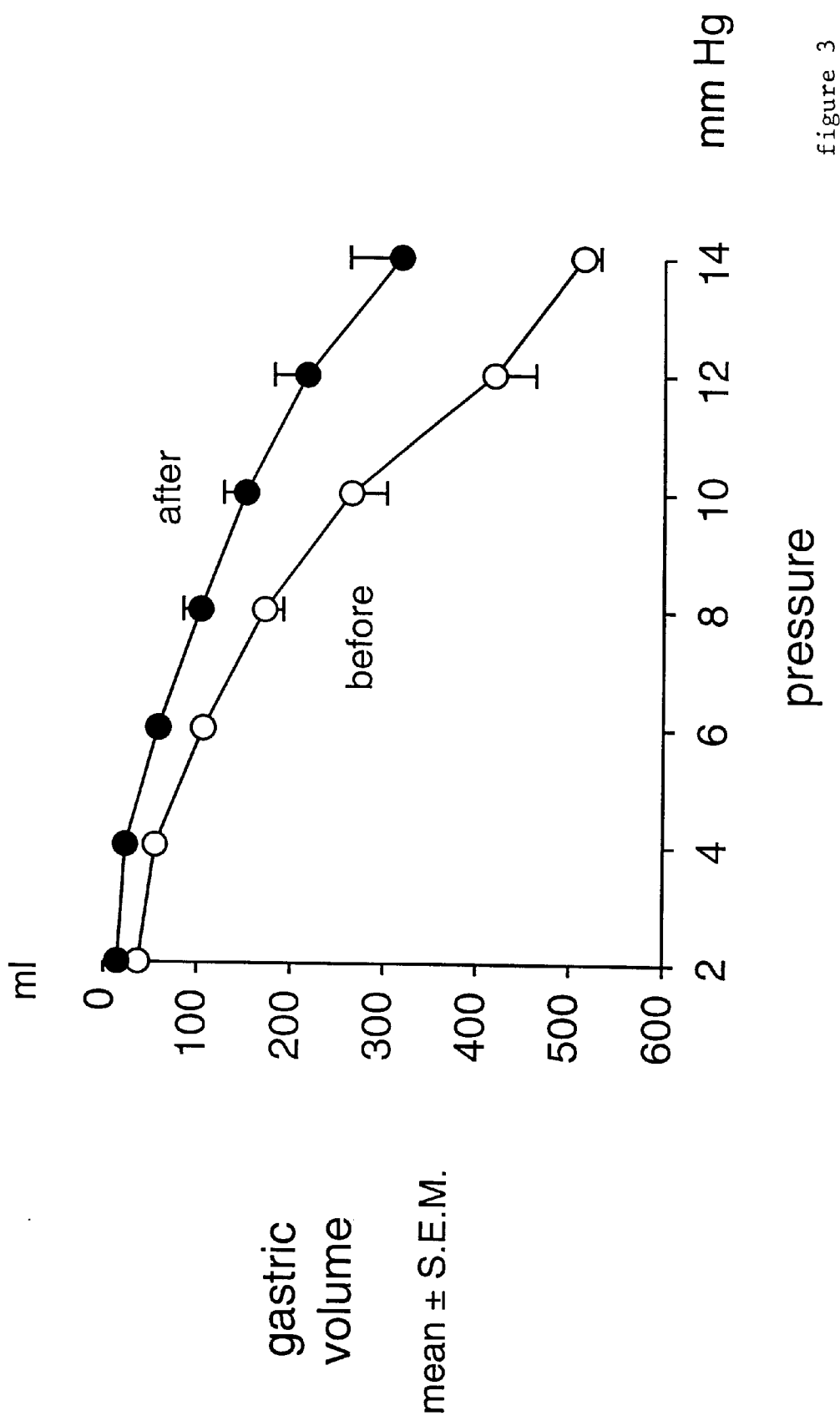
FIG. 3 Effect of paroxetine (0.63 mg/kg s.c.) on gastric relaxation induced by changes in pressure in conscious dogs. (n=4)
Figure 4:
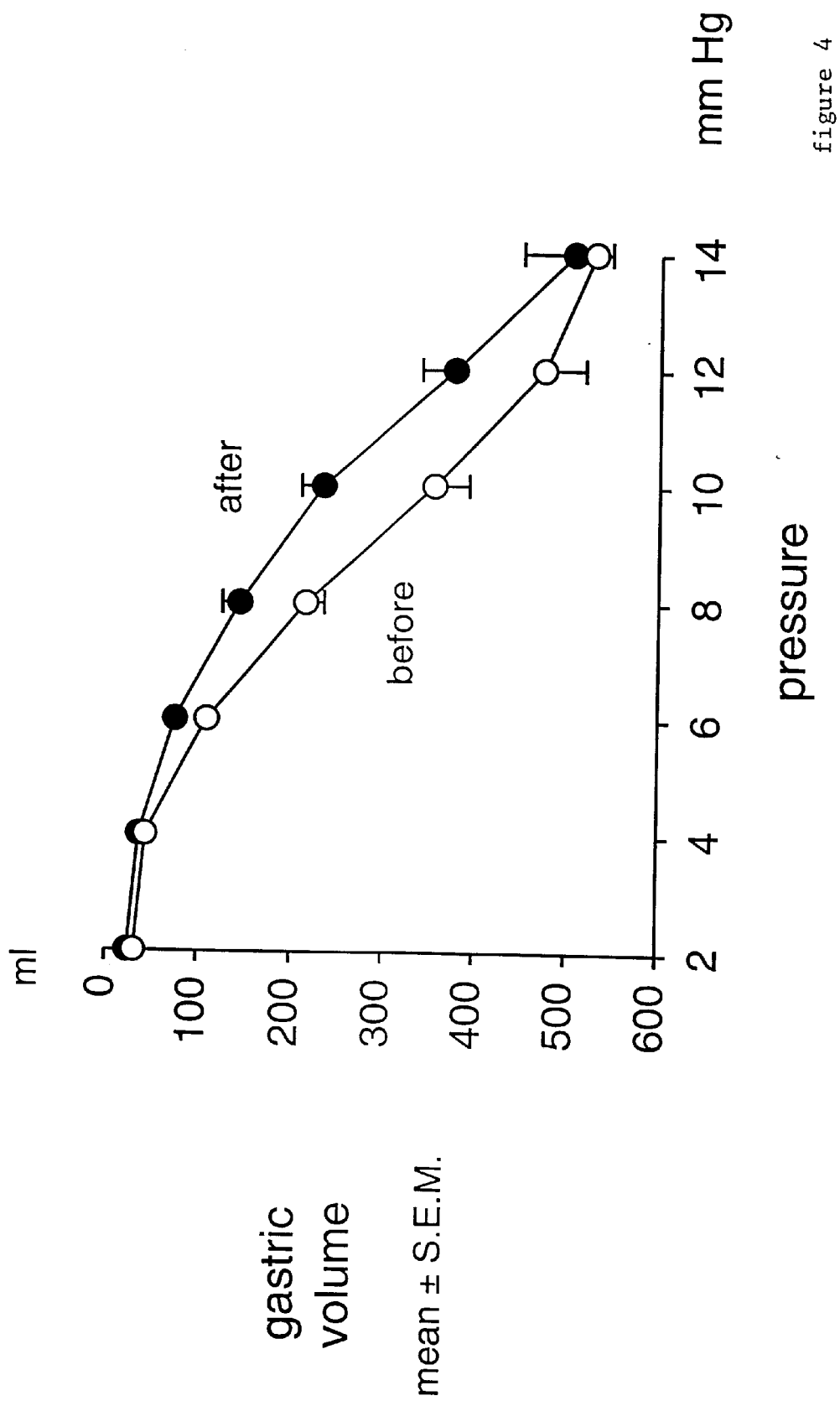
FIG. 4 Effect of fluoxetine(0.63 mg/kg s.c.) on gastric relaxation induced by changes in pressure in conscious dogs. (n=4)
Figure 5:
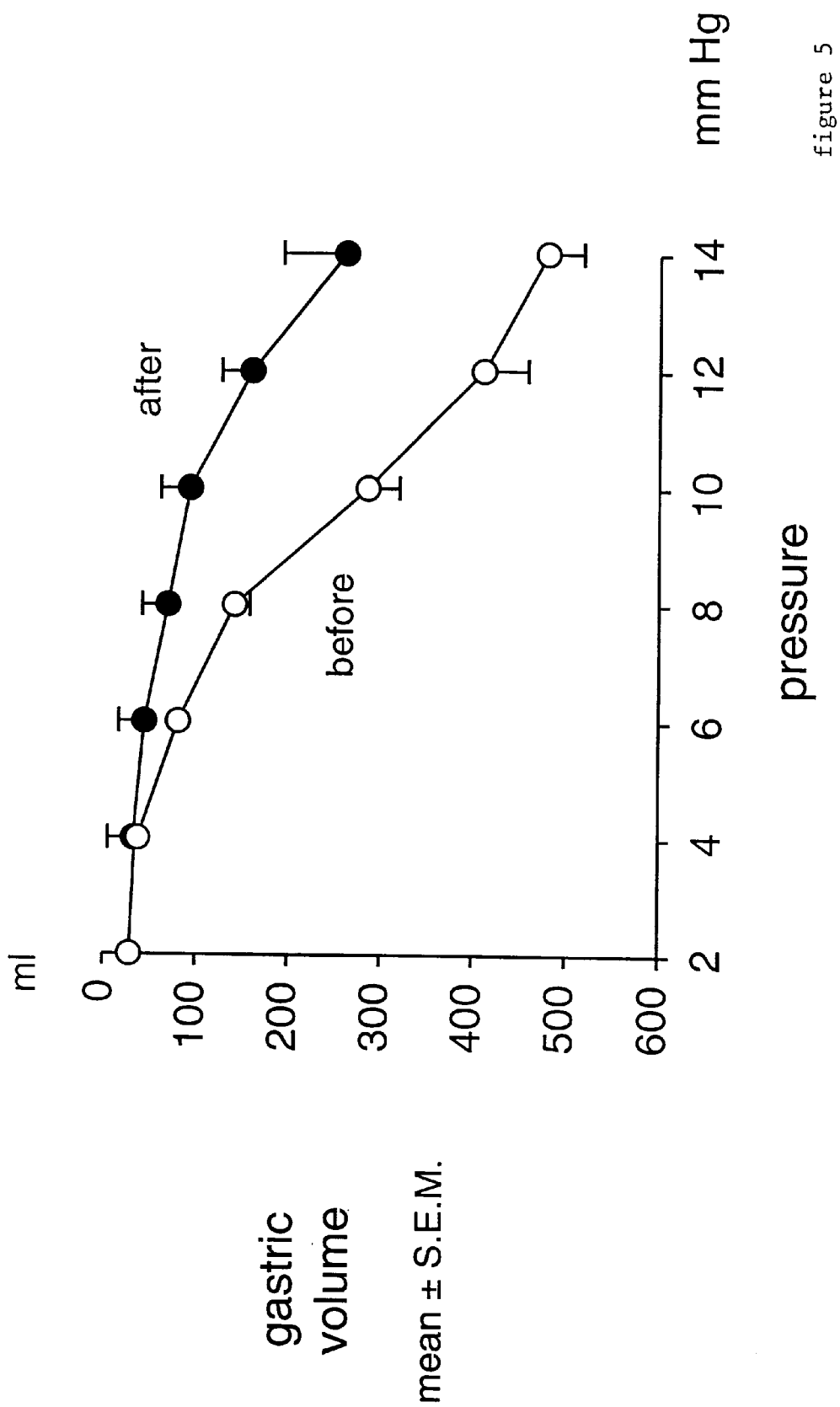
FIG. 5 Effect of CGP-6085-A (0.63 mg/kg s.c.) on gastric relaxation induced by changes in pressure in conscious dogs. (n=4)
Figure 6:
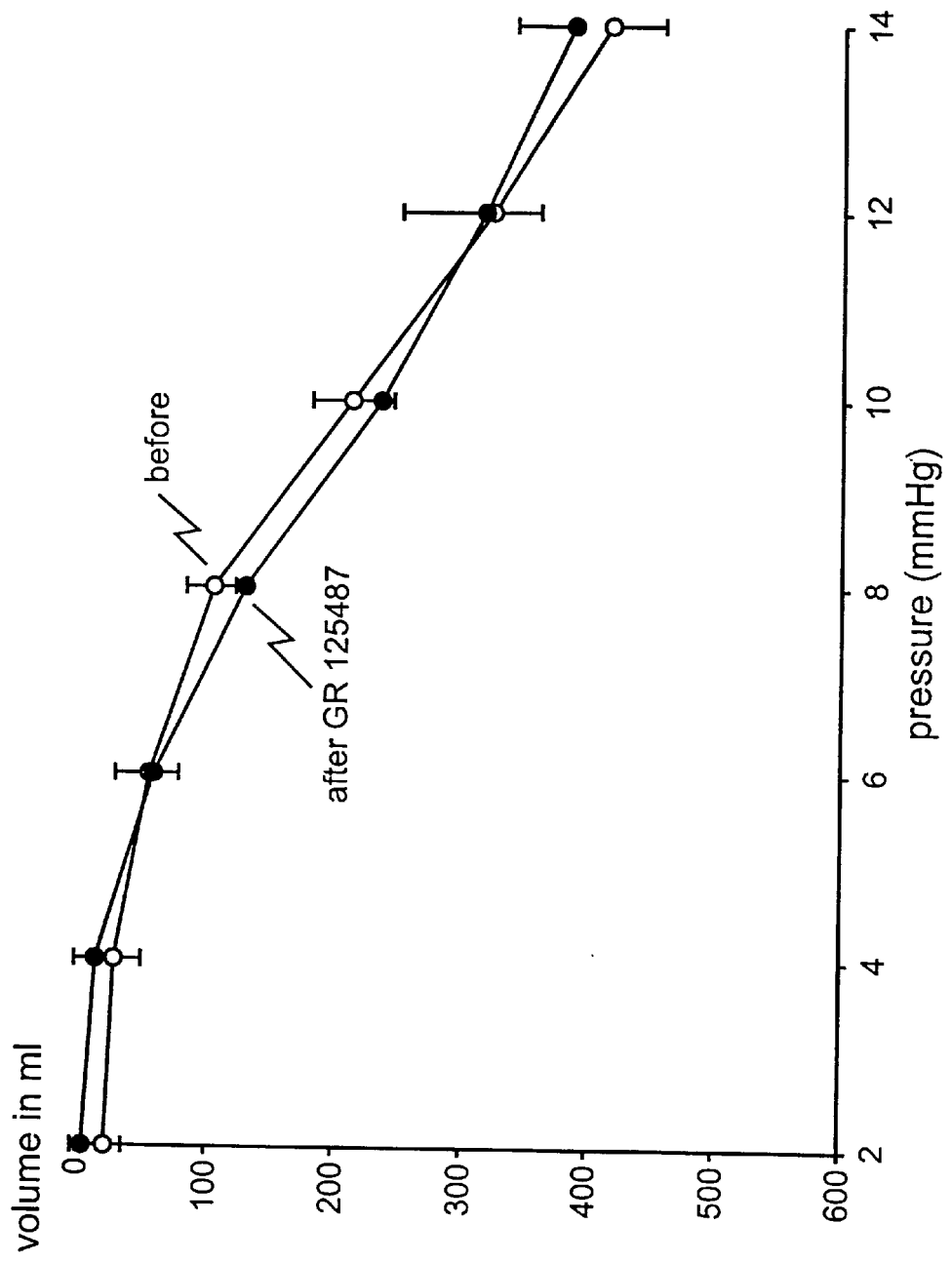
FIG. 6 Effect of GR 125487 on gastric relaxation induced by changes in pressure in conscious dogs. (n=4)
Figure 7:
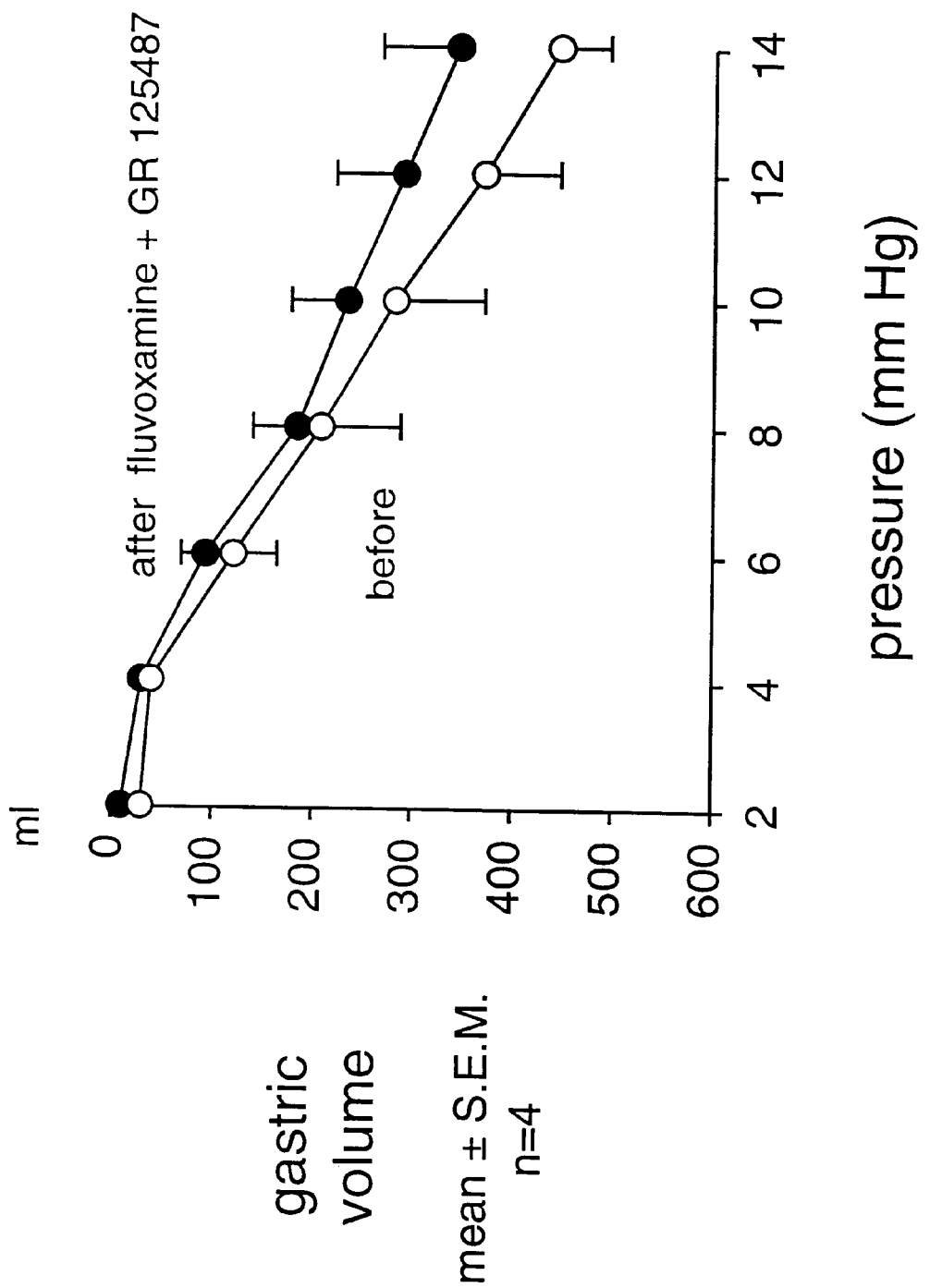
FIG. 7 GR 125487 antagonizes the effect of fluvoxamine on gastric relaxation induced by changes in pressure in conscious dogs. (n=4)
Figure 8:
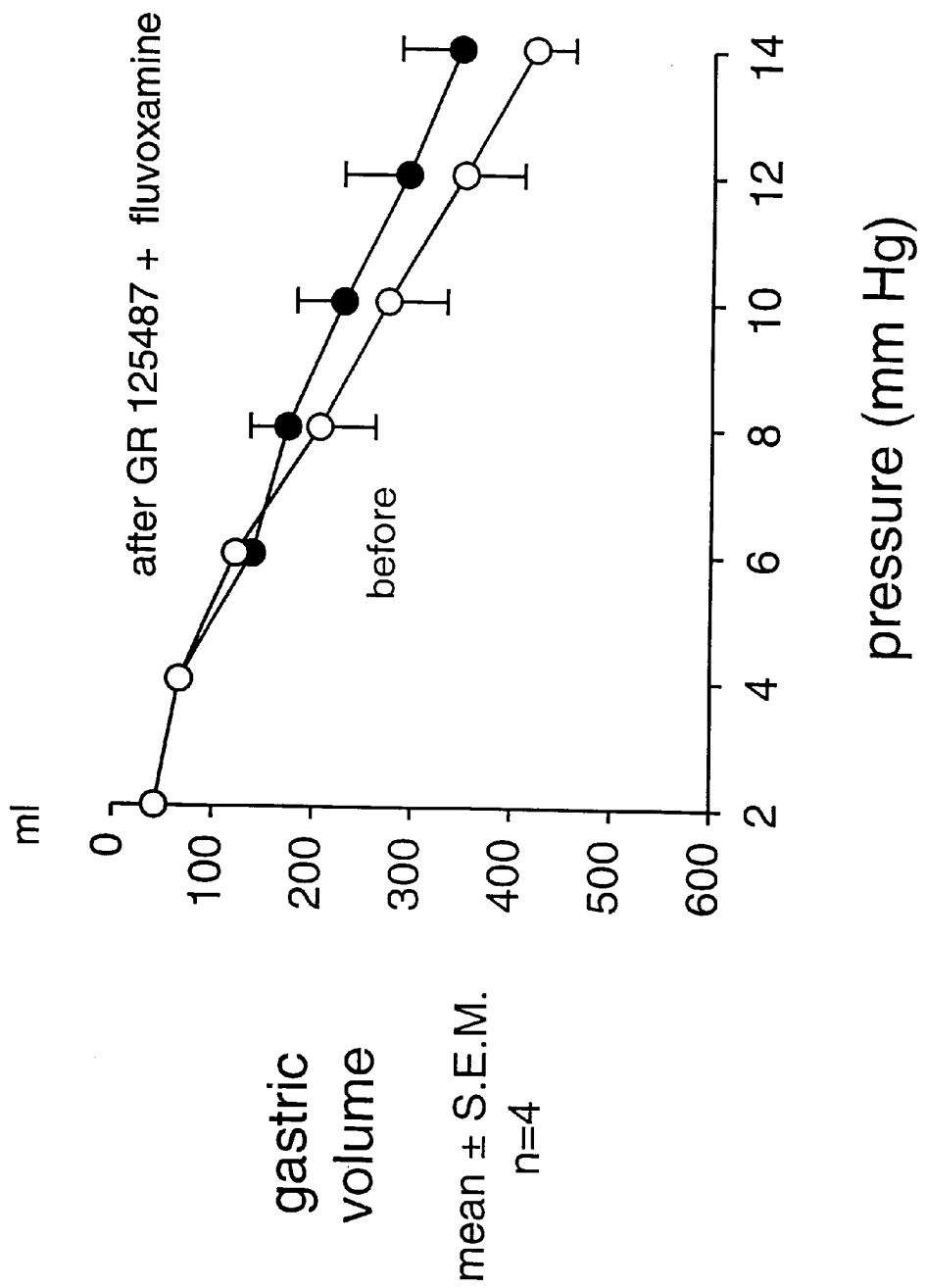
FIG. 8 Effect of fluvoxamine (0.63 mg/kg s.c.) in the presence of a GR 125487 on gastric relaxation induced by changes in pressure in conscious dogs. (n=4)

Hereinafter the term "A.I." refers to the combination of a 5HT4 receptor antagonist and a SSRI in a ratio of about 1/15 (5 HT4 receptor antagonist/SSRI)

Example D.1: Capsules 40 g of the A.I., 6 g sodium lauryl sulfate, 56 g starch, 56 g lactose, 0.8 g colloidal silicon dioxide, and 1.2 g magnesium stearate are vigorously stirred together. The resulting mixture is subsequently filled into 1000 suitable hardened gelatin capsules, each comprising 40 mg of the A.I.

Example D.2: Film-Coated Tablets

Preparation of Tablet Core

A mixture of 500 g of the A.I., 570 g lactose and 200 g starch is mixed well and thereafter humidified with a solution of 5 g sodium dodecyl sulfate and 10 g polyvinylpyrrolidone in about 200 ml of water. The wet powder mixture is sieved, dried and sieved again. Then there are added 100 g microcrystalline cellulose and 15 g hydrogenated vegetable oil. The whole is mixed well and compressed into tablets, giving 10.000 tablets, each comprising 50 mg of the active ingredient.

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinylpyrrolidone and 30 ml of concentrated colour suspension and the whole is homogenated. The tablet cores are coated with the thus obtained mixture in a coating apparatus.

We claim:

1. A method of avoiding, alleviating, suppressing or overcoming the gastrointestinal effects caused by a selective serotonin reuptake inhibitor comprising administering to a host in need thereof an effective amount of a 5HT4 receptor antagonist.

2. The method of claim 1 wherein the 5HT4 receptor antagonist is selected from A-85380, SB 204070, SB 207226, SB 207058, SB 207710, SB 205800, SB 203186, SDZ 205557, N 3389, FK 1052, SC 56184, SC 53606, DAU 6285, GR 125487, GR 113808, RS 23597, RS 39604, LY-353433 or R 50595.

3. The method of claim 1 wherein the selective serotonin reuptake inhibitor is selected from fluvoxamine, fluoxetine, paroxetine, sertraline, citalopram, venlafaxine, cericlamine, duloxetine, milnacipran, nefazodone, cyanodothiepin, CGP-6085-A, FG-7080, LY 280253, LY-285974 or RP 68303.

4. The method of claim 1 wherein the 5HT4 receptor antagonist is GR 125487.

5. The method of claim 1 wherein the selective serotonin reuptake inhibitor is fluvoxamine, citalopram, paroxetine, fluoxetine, CPG-6085-A.

6. The method of any of claims 2 to 5 and 1 wherein the gastrointestinal effect is nausea.

7. A pharmaceutical composition comprising a therapeutic amount of a selective serotonin reuptake inhibitor and an effective amount of a 5HT4 receptor antagonist and a pharmaceutically acceptable carrier.

8. A pharmaceutical composition as claimed in claim 7 wherein the selective serotonin reuptake inhibitor is fluoxetine.

9. A pharmaceutical composition as claimed in claim 7 wherein the 5HT4 receptor antagonist is GR 125487.

10. A process for preparing a pharmaceutical composition as claimed in claim 7 wherein a therapeutic amount of a selective serotonin reuptake inhibitor and an effective amount of a 5HT4 receptor antagonist are intimately mixed with a pharmaceutically acceptable carrier.

11. A product containing a 5HT4 receptor antagonist and a SSRI as a combined preparation for simultaneous, separate or sequential use in antidepressant therapy.

* * * * *